United States Patent [19]

Stout

[11] Patent Number: 5,774,950

[45] Date of Patent: Jul. 7, 1998

[54] TIE WITH CLIPS

[76] Inventor: Richard A. Stout, 78471 Cedar Park Rd., Cottage Grove, Oreg. 97424

[21] Appl. No.: 693,904

[22] Filed: Aug. 5, 1996

[51] Int. Cl.⁶ .................................................. A44B 21/00
[52] U.S. Cl. .................... 24/298; 24/3.13; 24/306
[58] Field of Search ........................ 24/298, 302, 306,
24/265 EE, 3.13; 248/104; 439/822, 506;
128/DIG. 15, DIG. 26

[56] References Cited

U.S. PATENT DOCUMENTS

| | | | |
|---|---|---|---|
| 580,293 | 4/1897 | Peterson | 24/265 EC |
| 2,110,037 | 3/1938 | De Rosa | 248/104 |
| 3,678,438 | 7/1972 | Gamson | 439/822 X |
| 4,308,642 | 1/1982 | Heyman | 24/306 |
| 4,972,859 | 11/1990 | Noviello, Jr. et al. | 132/273 |
| 4,979,707 | 12/1990 | McErlean | 248/104 |
| 5,083,732 | 1/1992 | Akamine | 248/104 |
| 5,135,189 | 8/1992 | Ghazizadeh | 248/104 |
| 5,192,041 | 3/1993 | Bryant | 248/104 |
| 5,459,903 | 10/1995 | Treacy | 24/3.13 |
| 5,489,075 | 2/1996 | Ible | 24/298 X |
| 5,603,479 | 2/1997 | Kristy | 248/104 |

*Primary Examiner*—James R. Brittain
*Attorney, Agent, or Firm*—James D. Givnan, Jr.

[57] ABSTRACT

A tie having a shapeable elongate member with alligator clips affixed to its ends. A jacket on the elongate member is of resilient material. A holder is attachable to a clip and includes tube engaging members to support the tube in place relative the patient. The holder has closure strips for tube retention. A supplemental tie is attachable to the clips on the first mentioned elongate member to assist in supporting articles adjacent the patent. A clip of the tie may be attached to the elongate member to provide an enclosure for confining two or more tubes.

2 Claims, 1 Drawing Sheet

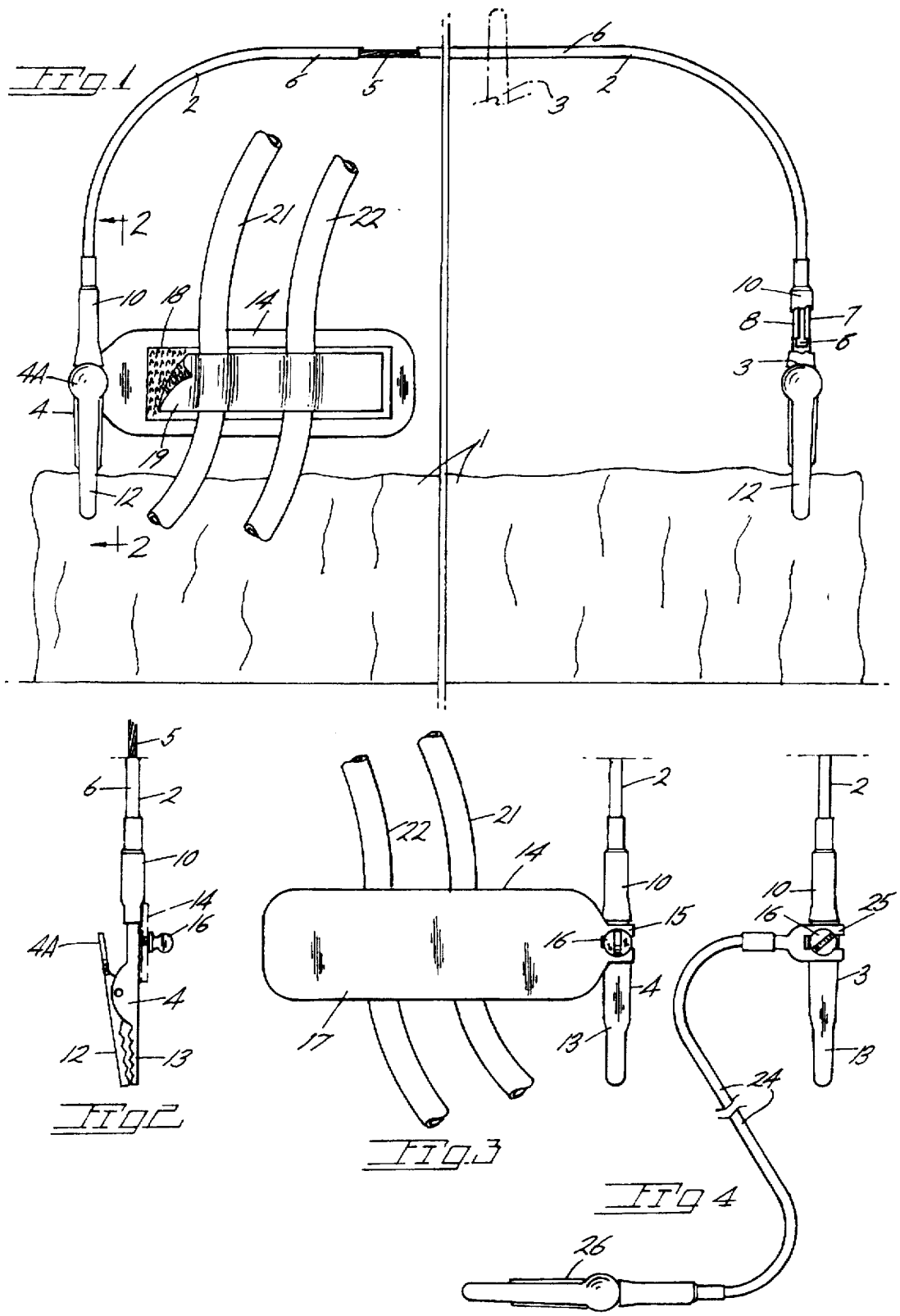

5,774,950

TIE WITH CLIPS

BACKGROUND OF THE INVENTION

The present invention pertains generally to ties for the joining of articles to one another.

Ties are widely used in the medical and dental fields for the joining of various items, as for example, gowns and bibs, in place on the patient. Typically such ties are of fabric construction and can not be shaped to facilitate attachment to the article being secured in place as such ties are devoid of any degree of rigidity.

Used in the dental field are bib ties formed from lengths of ball chain which, in similarity to fabric ties, have no degree of rigidity. A shortcoming with such ties is the difficulty in readily placing and attaching the tie in place. A further drawback to existing ties as found on various articles in the medical and dental field is the tendency of such ties to become tangled when, for example, gowns or other tie equipped articles are stacked for storage.

A problem exists in the bundling or joining of medical tubing, as for example, IVs and drainage tubes which readily become dislodged during movement of the patient. Typically it is a common practice to tape tubing serving a patient which complicates the task of tube separation and tube detachment from the patient. Further, the taping of tubes in place is time consuming and, not uncommon, may have to be done repeatedly.

The use of ball chain for a tie is undesirable in that such chains tangle easily, are difficult to clean, and can not be shaped to facilitate tie attachment. The aspects of sanitizing a ball chain are unknown.

SUMMARY OF THE INVENTION

The present invention is embodied within a tie having a malleable core which facilitates manipulation of the tie during attachment of clips at the ends to an article.

A malleable core extends substantially the length of the present tie and terminates at its ends in engagement with clips having spring biased jaws. The malleable core of the tie is preferably jacketed to provide an impervious cover to permit sanitizing of the tie and the color coding of ties of different lengths. Protective sleeves snugly enclose end segments of the tie and a portion of each clip and accordingly the present tie lends itself to being sanitized as by being wiped with an anti-bacterial disinfectant or gas sanitization. A holder may be coupled to a clip of the present tie with closure members on the holder serving to retain medical or dental items, as for example, tubing heretofore held in place by tape. A jacket in place about the core of the tie is of a resilient nature and permits secure engagement of a tie clip to permit the tie to be used for bundling a collection of tubes. The holder is coupled to the tie by fastener means which permits convenient installation and removal of the holder.

Important objectives of the present invention include the provision of a tie for various uses, particularly in the medical and dental fields, to facilitate attachment of various items including ice packs and bulky dressings to the patient; the provision of a tie having a malleable core and resilient jacket thereabout allowing pre-shaping of the tie prior to tie use with resilient coating rendering the tie easily sanitized and color coded for different lengths; the provision of a tie having spring biased clips and with a semirigid elongate member enabling positioning of a clip for convenient attachment to an article; the provision of a tie having a malleable core and a resilient jacket thereabout with clips partially enclosed within its sleeves which may be shrink wrapped to the clip and jacketed core; the provision of a tie which may be fitted with a holder, as for example, for retention of tubes heretofore held in place adjacent the patient by tape applied to the tubes and patient; the provision of a tie having a holder associated therewith which supports tubular segments by means of fabric closure members in place about said segments; the provision of a tie equipped with spring biased clips and with the tie having a resilient jacket to which one or both of the tie clips may be firmly attached to form a tube enclosure to retain tubes in compact bundles.

BRIEF DESCRIPTION OF THE DRAWINGS

In the accompanying drawings:

FIG. 1 is an elevational view of the present tie sectioned for purposes of illustration in use supporting a bib;

FIG. 2 is an elevational view of a clip of the present tie taken along line 2—2 of FIG. 1;

FIG. 3. is a rear elevational view of the clip and holder attached thereto shown in FIG. 1;

FIG. 4 is a plan view of a supplemental tie affixed to fastener elements of two clips.

DETAILED DESCRIPTION OF THE PREFERRED EMBODIMENTS

With continuing attention to the drawings wherein applied reference numerals indicate parts similarly hereinafter identified, the reference numeral 1 indicates an article such as a bib of the type worn by a medical or dental patient. It will be understood that the present tie may be utilized for various diverse uses, including a clip for holding a hospital gown closed, supporting bulky dressings or ice packs, medical tubing containment as well as other purposes which will be apparent to users of the tie.

With attention to the present tie, an elongate flexible member at 2 serves to join clips at 3 and 4. The elongate flexible member includes a wire core 5, preferably formed from braided copper wire strands which may be readily shaped by the user to facilitate tie installation. A jacket or covering 6 of the tie is of resilient nature to the extent later described clips may be securely engaged. Such jacketed wire may be of the type used in electrical wiring installations. The end segments of elongate member 2 are secured to the clips 3 and 4 by bite defining flanges 7 and 8 of each clip being crimped to the end segment. Such an attachment of elongate member 2 to a clip is thereafter enclosed by a sleeve 10 which may be of heat shrink material to effect enclosure of the end segment and the engaged portion of the clip. Sleeve 10 being in snug engagement with the elongate member and with the attached portion of the clip contributes to the present tie being easily sanitized.

A suitable clip 3-4 for the present tie is that known in the electrical trade as an alligator clip having serrated jaws biased toward one another by a coil spring (not shown) with a finger tip receiving pad as at 4A enabling opening of the clip. As typically shown in FIG. 2, clip jaws at 12 and 13 are serrated to provide toothed edges for spring biased gripping engagement with an article.

With attention to FIG. 1 and FIG. 3, a holder 14 is disclosed having a bifurcated end 15 for engagement to a clip by means of a threaded fastener 16 which may be a shouldered thrumb screw to provide adequate bearing surface for holder engagement. The holder has an elongate base 17 and is preferably of a pliable synthetic material. Affixed as by an adhesive backing to holder base 17 is a fabric closure strip or member 18 to which adheres a companion closure member 19. The fabric closure strips may be of the type having loops and flexible hook elements. Such material is manufactured and sold under the registered trademark VELCRO. The present holder snugly confines flexible tubes 21 and 22 for medical or dental purposes. The strips, when urged into snug engagemnt with the tubing, confine the tubing against slipping but permit intentional adjustment of the tubing relative the holder. While only one surface of holder 17 is shown in use, it will be understood that both surfaces of the holder may be utilized for tube retention.

With attention to FIG. 1, clip 3 is shown in fragmentary form and in broken lines in gripping engagement with elongate member 2 to provide an enclosure which may extend about multiple tubes to confine same in an orderly bundle. The teeth of the serrated jaws 12 and 13 of the clip, when biased into jacket 5, provide for secure attachment of clip 3.

As shown in FIG. 4, the present tie may be provided with a supplemental tie having an elongate member 24 having one end segment provided with a flat connector 25 for securement by threaded fastener 16 to a clip 3 or 4. The remaining end of the supplemental tie terminates in a clip 26 of the type above described. Supplemental tie 24 is useful when it is necessary to support a bulky dressing or large cold or hot pack against the body of a patient. Both the primary flexible member 2 and the supplemental elongate flexible member 24 may be shaped to accommodate the item being supported thereby to contribute to support of same in a secure manner.

While I have shown but a few embodiments of the invention, it will be apparent to those skilled in the art that the invention may be embodied still otherwise without departing from the spirit and scope of the invention.

Having thus described the invention, what is desired to be secured by a Letters Patent is:

I claim:

1. A combination tie assembly and tube holder for attachment of an article to a patient and comprising, first and second finger actuated clips each having spring biased jaws and a finger tip pad, an elongate shapeable member including a malleable core and having opposite end segments individually secured to said clips, said tube holder comprising cooperating fabric closure strips engageable with one or more flexible tubes, a base, and fastener means on said first clip including a shoulder and attaching said base of the tube holder to said first clip.

2. The tie assembly claimed in claim 1 additionally including a supplemental tie having an elongate shapeable member with a connector at one end for attachment to said second clip by a threaded fastener on the second clip.

* * * * *